United States Patent [19]

Rodrian

[11] 4,455,610

[45] Jun. 19, 1984

[54] SELF-CONTAINED ESTROUS DETECTION TAG

[76] Inventor: James A. Rodrian, 1123 Lake Shore Rd., Grafton, Wis. 53024

[21] Appl. No.: 345,580

[22] Filed: Feb. 4, 1982

[51] Int. Cl.³ .............................................. A61B 5/10
[52] U.S. Cl. ....................................... 364/415; 119/1; 128/738; 377/6
[58] Field of Search ................ 364/415; 128/738, 782; 119/1; 377/6, 15, 39

[56] References Cited

U.S. PATENT DOCUMENTS

| | | | |
|---|---|---|---|
| 4,112,926 | 9/1978 | Schulman et al. | 128/782 |
| 4,117,834 | 10/1978 | McPartland et al. | 128/782 |
| 4,151,831 | 5/1979 | Lester | 364/415 X |
| 4,192,000 | 3/1980 | Lipsey | 364/415 |
| 4,247,758 | 1/1981 | Rodrian | 377/6 |
| 4,353,375 | 10/1982 | Colburn et al. | 128/782 |
| 4,367,527 | 1/1983 | Desjacques | 364/415 X |

FOREIGN PATENT DOCUMENTS 2058359  4/1981  United Kingdom .

Primary Examiner—David H. Malzahn
Attorney, Agent, or Firm—Barry E. Sammons

[57] ABSTRACT

A tag suitable for attachment to an animal includes a programmed microprocessor which monitors the activity of the animal. Activity is measured by counting the closures of a mercury switch, and when the current activity exceeds a reference activity by a preset amount, a light emitting diode is energized. Four light emitting diodes are provided to indicate four separate levels of activity.

11 Claims, 7 Drawing Figures

SELF-CONTAINED ESTROUS DETECTION TAG

BACKGROUND OF THE INVENTION

The field of the invention is systems for detecting and indicating estrus in animals, and more particularly, systems for electronically indicating estrus in dairy cows.

In my U.S. Pat. No. 4,247,758 I describe an electronic system for detecting estrus in animals. This system includes a transponder unit which is carried by the animal and which transmits a signal to a transceiver unit that indicates both the identity of the animal and its activity. The transceiver unit is positioned at a location which is frequented by the animal and it may be connected to a computer which analyzes the activity data and generates a report which indicates those animals that are in estrus.

Although my prior system operates quite satisfactorily, it is best suited for use on relatively large farms where many animals are involved and the fully automatic identification and estrous detection system is needed. The cost of this system cannot, however, be justified for many small farms, even though the need for accurate estrous detection may be just as great.

SUMMARY OF THE INVENTION

The present invention relates to a self-contained device which is carried by the animal and which provides a visual indication when the animal is in estrus. More particularly, it includes a motion detector for sensing significant animal movements, means for continuously maintaining a reference count which is indicative of the animal's average activity over a prior time period, means for counting the current activity of the animal, and means for providing a visual indication of estrus when the current detected activity exceeds a preset multiple of the reference activity.

A general object of the invention is to provide an economical means for automatically detecting estrus in animals. All of the circuitry is contained in a small housing in the form of a tag which is attached to the animal. No external computers or electronic apparatus are required.

Another object of the invention is to provide an estrous detection system which is easy to use. When applied to cows for example, the tag is strapped to a leg of the animal and reset by passing a magnet across the surface of the housing. The tag automatically monitors acitivity and when estrus is detected, a light is energized on the tag to notify the farmer. The tag may then be transferred to another animal and reset to monitor its activity.

Another object of the invention is to provide additional information for use in experimental and test applications. By employing a microprocessor in the tag to perform the necessary calculations, electronic communication can be added at nominal cost. The activity of the animal may then be accumulated over short time intervals and stored in a table to provide an activity profile of the animal over a long time interval. This activity data may be read from the tag using the communication routine programmed into the microprocessor.

Another object of the invention is to provide an estrous detection tag which is easy to manufacture. By employing a programmable microprocessor, the tag can be easily adapted to different applications merely by making slight program changes or changes to the parameters employed by the program. In addition, test and diagnostic features can easily be added at nominal cost.

Another object of the invention is to provide an estrous detection tag which has an extended useful life. The microprocessor and associated gates employ CMOS technology which consumes minimal power from the battery contained in the tag. In addition, the microprocessor is programmed to revert to a wait state in which it consumes even less power during intervals when no processing is required.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
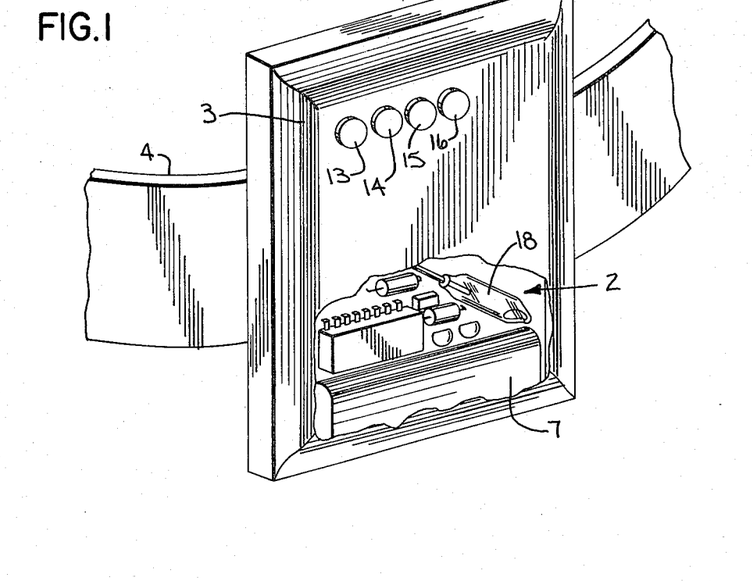
FIG. 1 is a perspective view with parts cut away of a tag which incorporates the present invention.

Referring particularly to FIG. 1, the tag 1 of the present invention includes a circuit board 2 which is enclosed in a molded plastic housing 3. The housing 3 is attached to a flexible strap, or belt 4 which may be attached around an appendage on the animal being monitored. In the case of dairy cows, the strap 4 is designed to attach securely to the hind leg of the cow. The interior of the housing 3 is completely filled with a potting compound to retain the circuit 2 and the electrical components.

Figure 2:
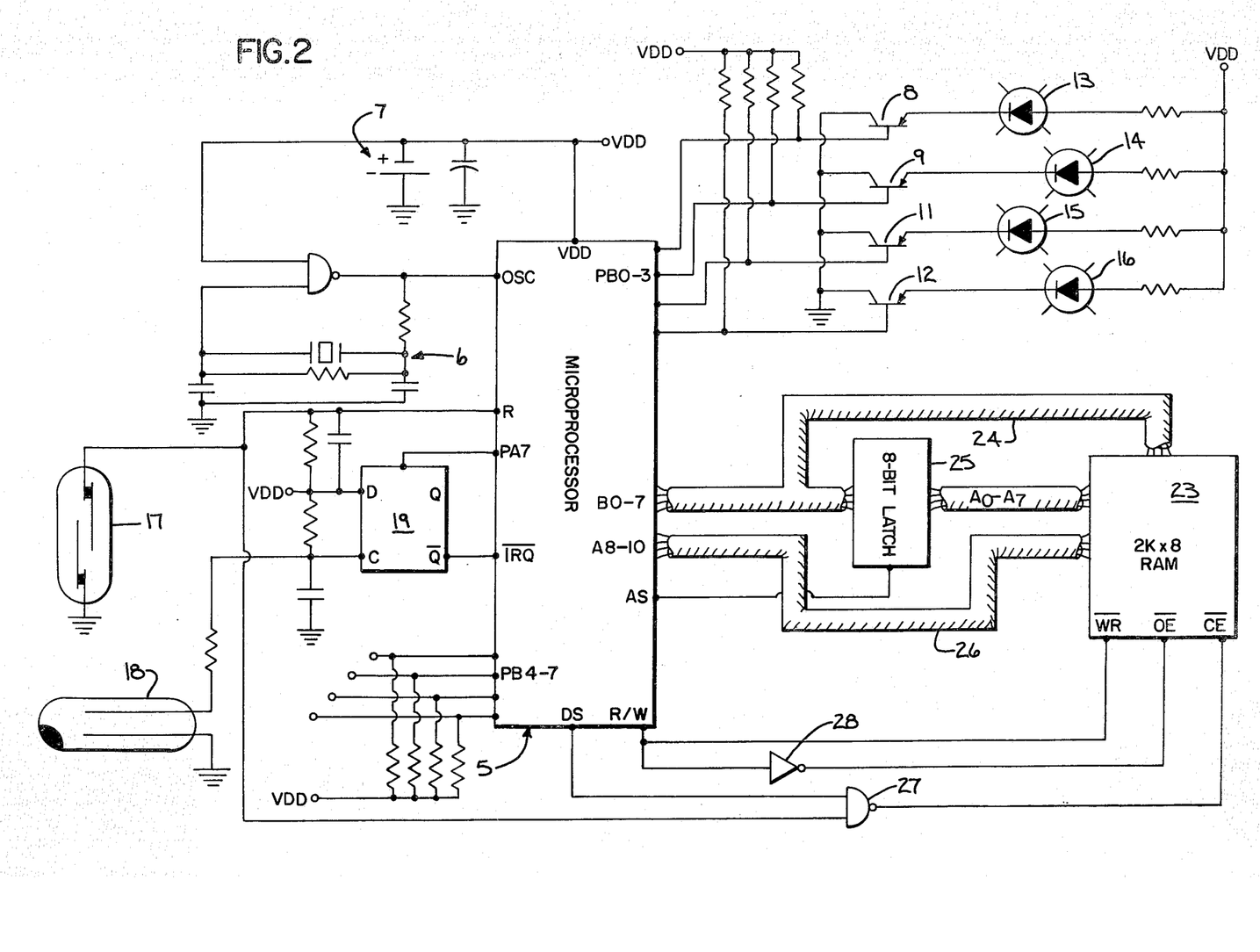
FIG. 2 is an electrical schematic diagram of the tag of FIG. 1.

Referring particularly to FIG. 2, the circuitry on the circuit board 2 is structured about an 8-bit microprocessor 5 which is driven by a 32.768 kHz clock circuit 6. Power is provided to the microprocessor 5 and the remaining circuit elements by a 1.7 ampere-hour lithium battery 7 which provides 3.7 volts at a terminal VDD. The model MC146805E2 microprocessor 5 is employed and it is manufactured by Motorola Inc. using CMOS technology. It draws very little current, and in addition, the microprocessor 5 may be placed into a "wait" state in which it draws approximately 40 microwatts of power. This feature is employed in the preferred embodiment to obtain a battery life of from three to four years.

Referring particularly to FIGS. 1 and 2, the microprocessor 5 has an 8-bit I/O port B which can be configured to input or output data under program control. Four leads of this B port (PB0-PB3) are configured as outputs and are connected to respective driver transistors 8-12. The transistors 8-12 provide amplification which enables the outputs PB0-PB3 to energize respective light emitting diodes (LED) 13-16. The LEDs 13-16 extend through the housing 3 where they may be easily seen and provide a visual indication of the extent of the animal's activity. The LED 13 provides a means for outputting more extensive data as will be described in more detail below.

The leads PB4-PB7 of the B port are configured to input data to the microprocessor 5 during production and testing of the tag 1. Lead PB4 is driven low by an external source to place the system in a "test" mode and lead PB5 is driven low by an external source when data is to be entered into the microprocessor. The serial data string is applied to lead PB7 and the microprocessor 5 is programmed to read this input data each time a negative voltage transition occurs in a clock signal which is applied to input lead PB6.

Referring particularly to FIG. 2, the microprocessor 5 is reset each time its reset terminal (R) is pulled to a logic low voltage. This is accomplished by a normally open reed switch 17 which connects to circuit ground. When a magnet is brought near the tag 1, its magnetic field closes the contacts in the reed switch 17 to perform the reset function. It is contemplated that the user will perform this reset function whenever one of the LEDs 14-16 is energized. As will be explained in more detail below, when a reset occurs the microprocessor 5 is vectored to a reset program which is executed to initialize the system and to perform a number of other functions.

Figures 3C, 3D:
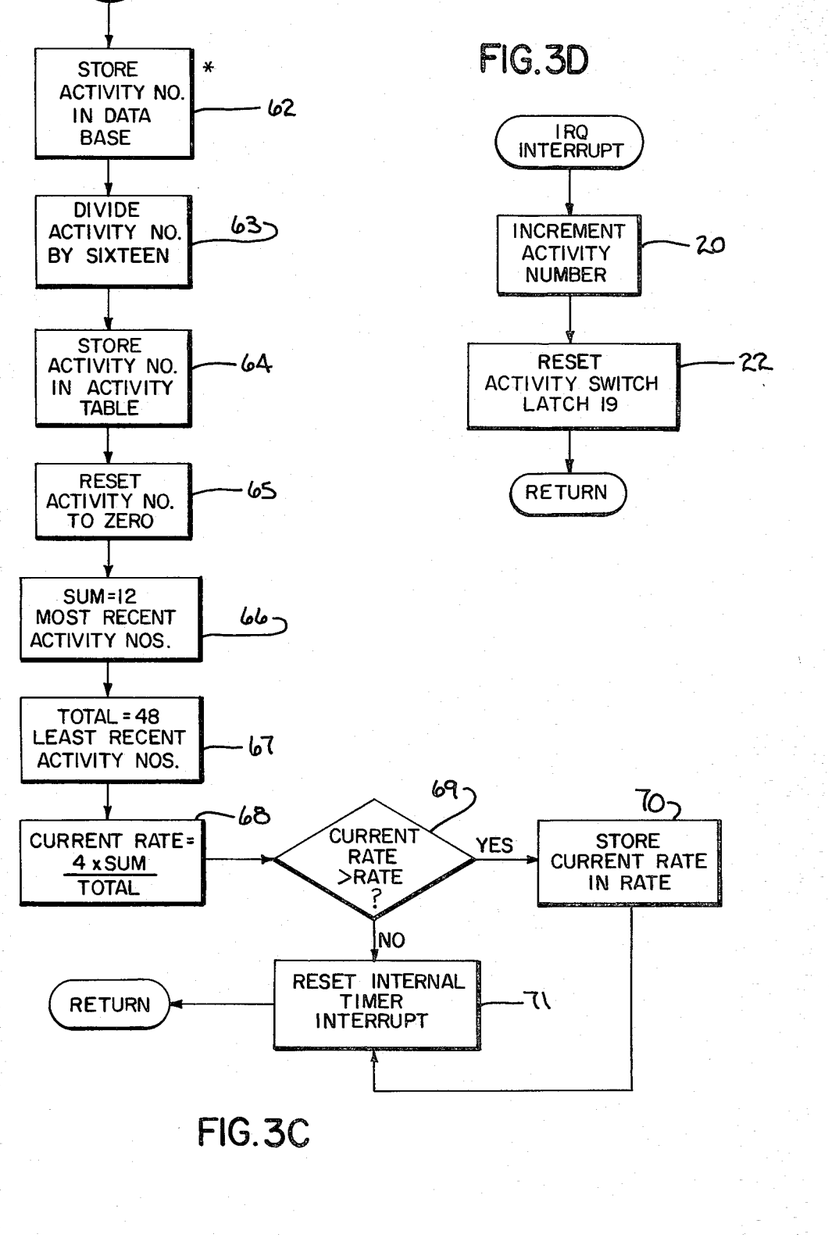
Figure 4:
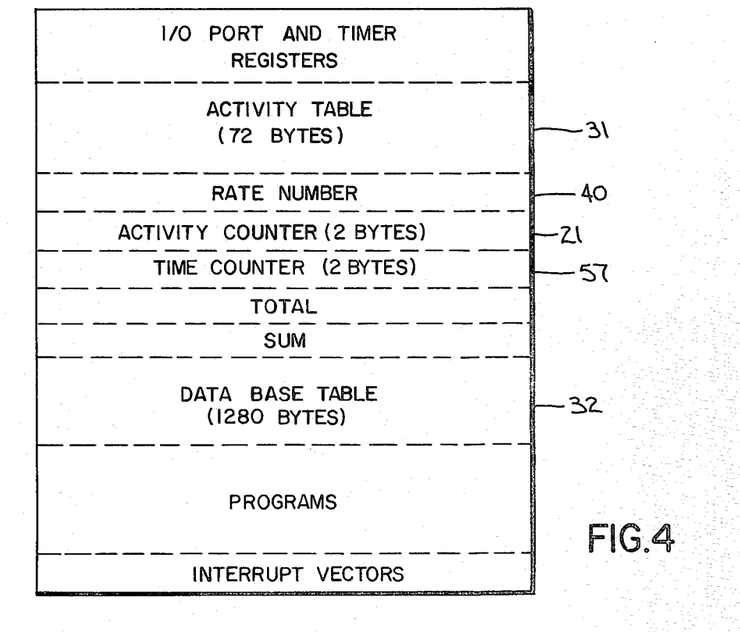
FIG. 4 is a memory map which illustrates the data structures employed by the programs of FIG. 3.

The activity of the animal to which the tag 1 is attached is detected by a mercury switch 18. One lead of the switch 18 is connected to circuit ground and the other lead connects to the clock input of a D-type flip-flop 19. The flip-flop 19 has its D input connected to a logic high voltage, and it operates as a latch which generates a logic low voltage at its $\overline{Q}$ output each time the mercury switch 18 closes. The latch 19 connects to an IRQ interrupt lead on the microprocessor 5, and with each mercury switch closure, the microprocessor 5 is vectored to an IRQ interrupt program. As shown in FIGS. 3D and 4. the IRQ interrupt program contains instructions indicated by process block 20 which increment an activity number counter 21. In addition, instructions indicated by process block 22 are executed to reset the latch 19 through the microprocessor's output port PA7.

Referring again to FIG. 2, the microprocessor 5 contains sufficient on-chip memory to store data for normal applications of the tag 1. However, it is contemplated that the tag 1 will also be used in experimental programs in which the activity of the animal may be recorded over extended periods of time. Accordingly, provision is made for the addition of an external random access memory (RAM) 23 which may store additional activity data. A 2K×8 CMOS RAM manufactured by Hitachi as the HM6116LP-4 is employed in the preferred embodiment. The RAM 23 is connected to an 8-bit data bus 24 which is driven by a bidirectional, multiplexed address/data port (leads B0-B7) on the microprocessor 5. These same leads B0-B7 serve to generate the lower eight bits of an address when a microprocessor address strobe terminal (AS) is at a logic high voltage, and this address data is stored in a latch 25 for application to the RAM 23. The three most significant address bits are generated at microprocessor address leads (A8-A10) which are connected directly to the RAM 23 by bus 26. The RAM 23 is enabled by a NAND gate 27 when a data strobe lead (DS) on the microprocessor 5 goes high, and data is then written to an addressed RAM location when a microprocessor read/write lead (R/W) goes to a logic low voltage. Data is read from an addressed location in the RAM 23 when the R/W lead goes high and an inverter gate 28 drives the output enable lead (OE) on the RAM 23 to a logic low voltage.

The microprocessor 5 executes stored program instructions to perform a number of functions. The assembly language listings of these stored programs are provided in Appendix A and flow charts of these programs are illustrated in FIGS. 3A-3D. As indicated above, two versions of the tag 1 are contemplated. The first version is for normal applications in which an animal activity profile over a sixty hour period is stored in the tag and employed to detect estrus. When estrus is detected one of the LED indicators 14-16 is energized. The second version of the tag is for experimental use. This second version stores a much longer animal activity profile and it provides a number of communicating features which will be described in more detail below. In the following description, the second version of the tag is illustrated, and asterisks denote those portions of the programs which may be deleted to form the first version of the tag.

Figure 3A:
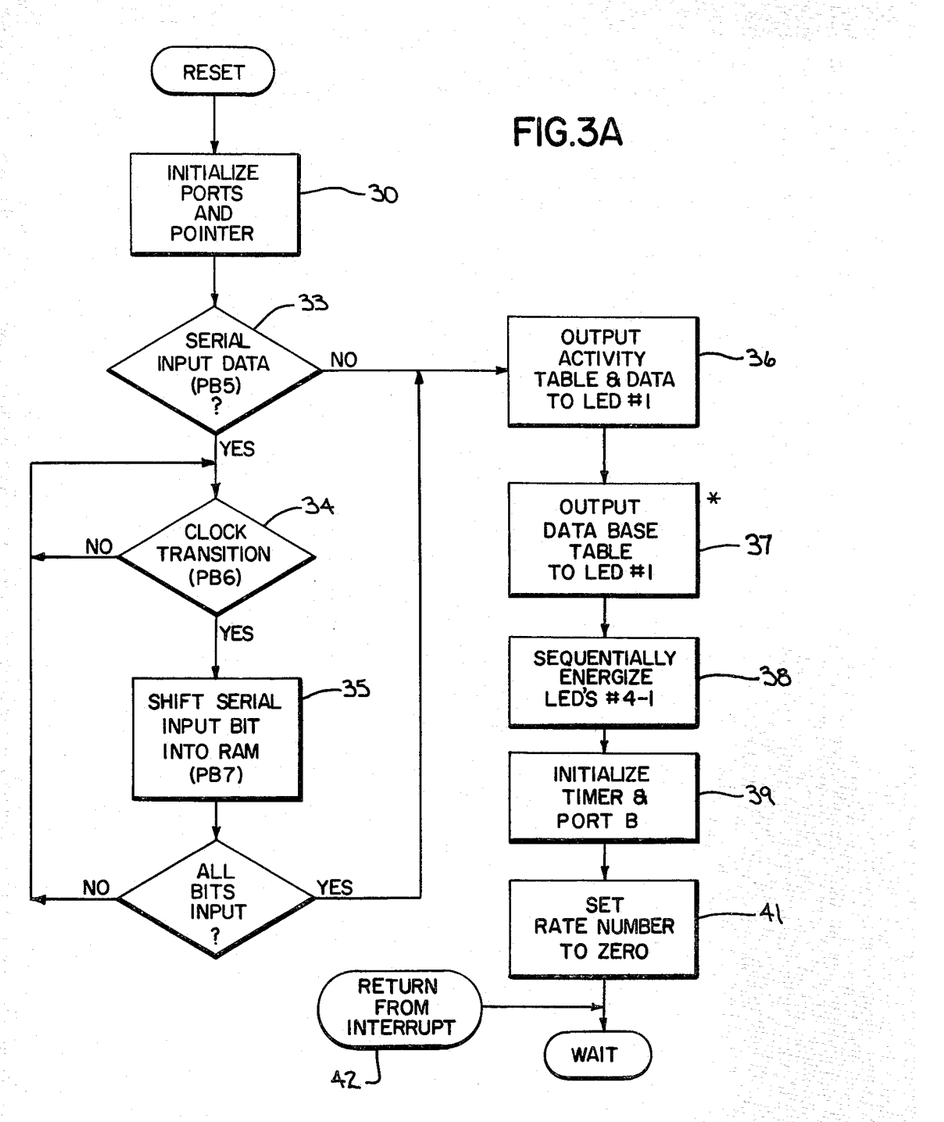
FIGS. 3A-3D are flow charts of the programs which are executed by the microprocessor in FIG. 2.

Referring particularly to FIGS. 3A and 4, each time a magnet is brought near the tag 1 the read switch 17 is closed and a reset program is executed. As indicated by process block 30, this program initializes the microprocessor's A and B ports, as well as a pointer to an activity table 31. The status of microprocessor input lead PB5 is then tested, as indicated by decision block 33, to determine if data is to be input into the system. If so, a loop which includes decision block 34 and process block 35 is entered and data is input through microprocessor input lead PB7 and stored in its internal RAM. Such data is entered during manufacture of the tag and may include a serial number and date which uniquely identifies the tag, as well as key parameters which customize the tag to the particular animals being monitored. Under normal operating conditions, however, the reset program branches at decision block 33 and no input data is received.

Referring still to FIG. 3A, the reset program outputs the animal's activity profile data from the activity table 31, as indicated by process block 36. This is accomplished by writing the data serially to the output lead PB0 which drives the LED 13. The LED 13 is thus energized to indicate a logic "0" and is deenergized to indicate a logic "1". An instrument (not shown in the drawings) may be coupled to the tag 1 to read this serial data which is output through the LED 13. In addition to the activity table data, other data such as diagnostic information may be output, or as indicated by process block 37, the much larger animal activity profile stored in the data base table 32 may also be output. In any case, each of the LEDs 13-16 is then momentarily energized as indicated by process block 38 to insure that they work properly, and further initialization is performed as indicated at process block 39. A "rate number" 40 is then reset to zero as indicated at process block 41, and a WAIT instruction is then executed to place the microprocessor 5 in its low-power wait state. In this wait state the microprocessor's internal timer continues to operate and the microprocessor 5 is responsive to the IRQ interrupt, timer interrupt and a reset interrupt. After a timer interrupt or an IRQ interrupt is serviced, however, the system returns at 42 and is again placed in the low-power wait state.

As indicated above, the IRQ interrupt occurs each time the mercury switch 18 closes. The IRQ interrupt service routine (FIG. 3D) merely increments the activity number counter 21 and resets the latch 19 before returning to the wait state. This event occurs each time the animal moves sufficiently to bring the mercury bead in the switch 18 into contact with its internal leads. The number of such movements are accumulated in the two-byte activity counter 21.

Figure 3B:
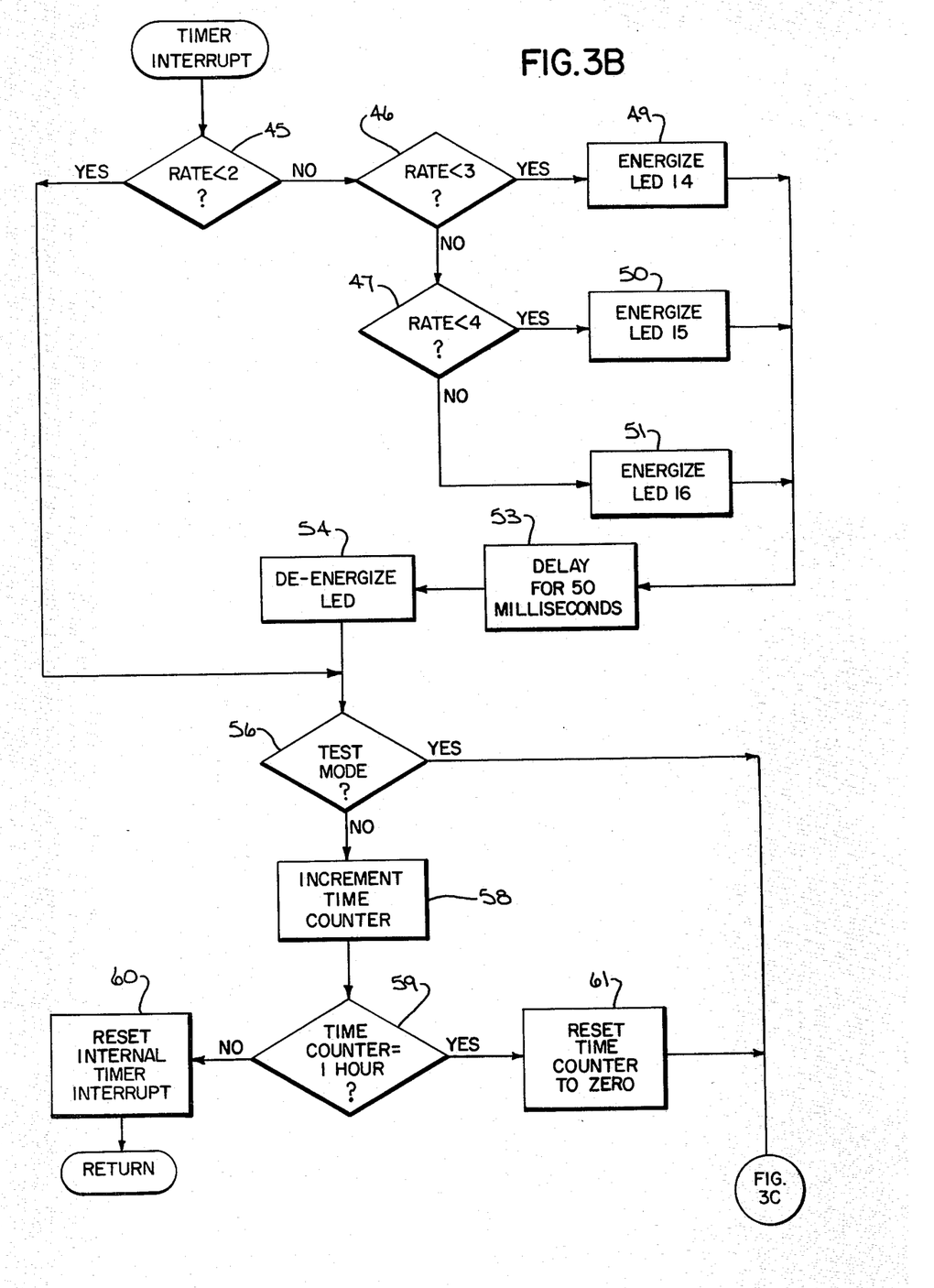

Referring to FIG. 3B, the internal timer in the microprocessor 5 is initialized to generate a timer interrupt every 2.5 seconds. As indicated by decision blocks 45–47, when this interrupt occurs the system is vectored to the timer interrupt service routine which examines the current value of the rate number 40. As will become apparent from the description below, the rate number is indicative of the activity of the animal over a recent time period as compared to the activity of the animal over a longer reference period. When the rate number is less than two, as determined at decision block 45, the animal's current activity is not noteworthy. Otherwise, one of the LEDs 14–16 is energized, as indicated by process blocks 49–51, to provide a visual indication that noteworthy activity is occurring. The appropriate LED is energized for 50 milliseconds, as indicated by process blocks 53 and 54, but because the timer interrupt occurs every 2.5 seconds, the energized LED blinks continuously. Only one of the LEDs 14–16 is energized at any time, and by observing which LED is illuminated, the relative increase in animal activity can be easily determined. Although the absolute activity which indicates estrus will vary from animal to animal, it has been found that a significant relative increase in animal activity is an accurate indication of estrus.

Every hour the rate number is recalculated to provide an updated indication of animal activity. Referring particularly to FIGS. 3B and 3C, the state of input lead PB4 is tested at decision block 56 to determine if the tag is undergoing testing. If not, a time counter 57 is incremented as indicated at process block 58 and the value of this counter 57 is then checked to determine if an hour has elapsed. If not, the system branches at decision block 59, the internal timer is reset at process block 60, and the system returns to the wait mode for another 2.5 seconds. If a one hour "sample" period has elapsed, the time counter 57 is reset at process block 61 and a new rate number is calculated. It should be apparent that the test mode of operation merely bypasses the one hour time requirement for recalculation of the rate number, and this feature merely enables the tag to be quickly tested.

Referring particularly to FIG. 3C, before calculating a new rate number the animal activity profiles are updated with the most current activity number. As indicated by process block 62, the contents of the activity counter 21 is first stored in the activity data base table 32. The same number is then divided by sixteen, as indicated by process block 63, to form a single byte result which is stored at process block 64 in the activity table 31. The activity counter 21 is then reset to zero at process block 65 to begin accumulating activity counts for the next hour.

As indicated at process block 66, the activity counts for the twelve most recent hours are then read from the activity table 31 and added together to provide a current activity value which is stored at "SUM". The value of the forty-eight least recent activity numbers are then read from the activity table 31 at process block 67 and added together to form a reference activity number which is stored at "TOTAL". The ratio of the current activity to the reference activity is then calculated at process block 68 to form the current rate number. If the calculated current rate is greater than the value stored as the rate number 40, the system branches at decision block 69 and updates the rate number 40 at process block 70. In either case, the internal timer is then reset at process block 71 and the system returns to the wait mode for another 2.5 seconds.

In the preferred embodiment the reference activity is calculated over a forty-eight hour period and the current activity is calculated over the most recent twelve hour period. These time periods can, of course, be easily changed to accommodate the activity patterns of various animals and breeds. Indeed, one of the purposes of the data base table option in the tag 1 is to store activity data over a much longer time period. This activity profile data can then be read out as described above, and studied to determine the optimal values of the "reference" and "current" time periods. The optimal values of these key parameters may be entered into the production tags which are to be employed on that particular animal breed.

Although the use of a microprocessor offers many advantages, it is also possible to construct a circuit which will emulate the functions described above. This and many other variations from the preferred embodiment described herein are possible without departing from the spirit of the invention.

Program Listing

```
;       ****    Constant and Parameter Definition   ****
;
PADAT:  EQU     0000H   ; RAM location of Port A data
PADIR:  EQU     0004H   ; RAM location of Port A direction register
PBDAT:  EQU     0001H   ; RAM location of Port B data
PBDIR:  EQU     0005H   ; RAM location of Port B direction register
TIMER:  EQU     0008H   ; RAM location of Timer
TIMCON: EQU     0009H   ; RAM location of Timer control register
;
;
        ORG     10H
;
ACTFIL: DS      48H     ; create space for 72 activity bytes
RATE:   DS      1H      ; calculated RATE
ACTHI:  DS      01H     ; number of switch closures since previous hour (16 bits)
ACTLO:  DS      01H
CRCHI:  DS      01H     ; high bits of CRC check bytes
```

```
CRCLO:   DS      01H             ; low bits of CRC check bytes
;
TWSEC:   DS      01H             ; 2.5 second counter
MIN:     DS      01H             ; minute counter
FLPNT:   DS      01H             ; activity file pointer
TOTHI:   DS      01H             ; total activity for previous 48 hours
TOTLO:   DS      01H
SUMHI:   DS      01H             ; total activity for previous 12 hours
SUMLO:   DS      01H
CNTR:    DS      01H             ; data counter
;
; These parameters are serially loaded at the time of manufacture.
;
SRNBR:   DS      06H             ; 6 bytes reserved for tag serial number and date
;                                  of manufacture
;
SECMAX:  DS      01H             ; maximum value for seconds up counter
MINMAX:  DS      01H             ; maximum value for minutes up counter
LMT1:    DS      01H             ; if 0 <= RATE < LMT1, then no LED blinks
LMT2:    DS      01H             ; if LMT1 <= RATE < LMT2, then LED 1 blinks
LMT3:    DS      01H             ; if LMT2 <= RATE < LMT3, then LED 2 blinks
LMT4:    DS      01H             ; if LMT3 <= RATE < LMT4, then LED 3 blinks
;                                  if LMT4 <= RATE, then LED 4 blinks
LEDON:   DS      01H             ; LED ON time (pulse width)
;
PRESCL:  DS      01H             ; Timer interrupt control and pre-scaler
ACTSHF:  DS      01H             ; activity count = activity count / (2**ACTSHF)
SUMSHF:  DS      01H             ; SUM = SUM * (2**SUMSHF)
SUMCNT:  DS      01H             ; number of previous activities to be summed together
FILTOP:  DS      01H             ; address of top of activity file in use
;
;
;
         ORG     0080H
;
         DB      'Copyright as an unpublished work by James A. Rodrian, 1981.'
;
;
; Routine which stores a sixteen bit activity count in the activity data base
; area of RAM (100H to 5FFH.)
; Required for research model only.
DATSTR:  LDA     ACTLO
INDXC:   STA     0100H           ; move Activity Count to data base
;
         LDA     INDXC + 2
         INCA                    ; increment data base pointer
         STA     INDXD + 2
;
         LDA     ACTHI
INDXD:   STA     0101H           ; move Activity Count to data base using Z-80
;                                  storage convention (LOW,HIGH)
;
         LDA     INDXD + 2
         INCA                    ; increment data base pointer
         STA     INDXC + 2
         BNE     STRRET          ; branch if ACCA is not 00
;
         LDA     INDXC + 1
         INCA                    ; increment data base pointer
         CMP     #06H
         BLO     STR1            ; branch if ACCA < 06H
;
         LDA     #01H            ; otherwise, reset data base pointer
STR1:    STA     INDXC + 1
         STA     INDXD + 1
STRRET:  RTS
;
;
;
         ORG     0600H
;
RESET:   LDA     #00H
         STA     PADAT           ; set all Port A bits LOW
;
```

```
            LDA     #0FFH
            STA     PADIR       ; set all Port A bits as output STA     PBDAT       ; set all bits of Port B HIGH LDA     #01H
            STA     PBDIR       ; set bit 0 of Port B as output
                                ; (for memory dump only)
            LDA     #6EH
            STA     TIMCON      ; stop counter - prevent CRC error
                                ; on first 256 bytes ; File pointer initialization may be required for initial Power ON condition LDA     FLPNT       ; check for 10H <= file pointer =< FILTOP
            CMP     #10H        ; check lower limit
            BLO     RST1        ; branch if pointer < 10H CMP     FILTOP      ; otherwise, check upper limit
            BLS     RST2        ; branch if pointer <= FILTOP RST1:       LDA     #10H
            STA     FLPNT       ; initialize file pointer to an acceptable value ; Routine used to store tag serial number and manufacturing date in RAM
;
;           Port B bit 5 = 0, routine is enabled
;           Port B bit 6 = HIGH to LOW transition, shift bit into RAM
;           Port B bit 7, data bit to be shifted into RAM RST2:       BRSET   5,PBDAT,RST7 ; if bit 5 = 1, serial IN is not being requested
            LDX     #SRNBR       ; load byte pointer RST3:       LDA     #08H         ; load bit counter
RST4:       BRSET   6,PBDAT,RST4 ; wait for HIGH to LOW clock transition
            ASL     PBDAT        ; move bit to Carry
            ROR     ,X           ; shift Carry to RAM
            DECA                 ; decrement bit counter
            BEQ     RST6         ; branch if 8 bits have been shifted in RST5:       BRCLR   6,PBDAT,RST5 ; wait for LOW to HIGH clock transition
            BRA     RST4         ; go back and shift in another bit RST6:       INCX
            CPX     #FILTOP+1    ; check if all bytes have been received
            BNE     RST3         ; branch if more bytes are to be shifted in ; Memory dump routine - locations 00H to FFH RST7:       LDX     #00          ; initialize pointer
            STX     CRCHI
            STX     CRCLO        ; initialize CRC check bytes XFER1:      LDA     ,X
            JSR     XMIT         ; serially transmitt the data LDA     ,X           ; get data byte
            ADD     CRCLO
            STA     CRCLO        ; add data to previous sum
            LDA     CRCHI
            ADC     #00H         ; increment high bits if carry was set by
                                 ; previous ADD

STA     CRCHI

INCX                 ; increment pointer
            BNE     XFER1        ; branch if 256 bytes have not been transmitted LDA     CRCLO        ; otherwise,
            JSR     XMIT         ; transmitt CRC check byte
```

```
            LDA     CRCHI
            JSR     XMIT            ; transmitt CRC check byte
;
;
            JSR     DUMP            ; 2K RAM MEMORY DUMP FOR RESEARCH ONLY
;
;
;
            LDA     #0FH
            STA     PBDIR           ; set Port B bits 3, 2, 1, & 0 as outputs
; LED test routine
;
            LDA     #0F7H           ; turn ON LED 4
            STA     PBDAT
            BRA     TSTLP2
;
TSTLP1:     ROR     PBDAT           ; turn one LED ON
TSTLP2:     LDA     #0FFH           ; load delay loop counter
TSTLP3:     DECA
            BNE     TSTLP3          ; branch if counter N.E. 0
            BRSET   0,PBDAT,TSTLP1  ; branch if LED 1 is not ON
;
            LDA     #00H
            STA     RATE            ; set RATE = 00
;
            LDA     #0FFH
            STA     PBDAT           ; turn all LED's OFF
;
            LDA     #00H
            STA     TIMER           ; set Timer = 00
            LDA     PRESCL          ; set Timer control register
;                                           bit 7 = 0, no interrupt pending
;                                               6 = 0, interrupt enabled
;                                               5 = 0, internal clock
;                                               4 = 0, disable external input
;                                               3 = 1, prescaler = 00
;                                               2, 1, 0 = 06H, 1/64 prescaler - one
;                                                       interrupt every 2.50 sec
            STA     TIMCON
;
LOOP:       WAIT                    ; all interrupts are enabled
;
            BRA     LOOP            ; jump to LOOP after an interrupt
;
;
; Routine for servicing a Timer interrupt
;
;
TIMINT:     LDA     RATE
            CMP     LMT1
            BLO     CLOCK           ; branch if RATE < LMT1
;
            CMP     LMT2
            BLO     LED1            ; branch if RATE < LMT2
;
            CMP     LMT3
            BLO     LED2            ; branch if RATE < LMT3
;
            CMP     LMT4
            BLO     LED3            ; branch if RATE < LMT4
;
LED4:       BCLR    3,PBDAT         ; otherwise, turn LED 4 ON
            BRA     ONTIME
;
LED3:       BCLR    2,PBDAT         ; turn LED 3 ON
            BRA     ONTIME
;
LED2:       BCLR    1,PBDAT         ; turn LED 2 ON
            BRA     ONTIME
;
```

```
LED1:    BCLR    0,PBDAT          ; turn LED 1 ON
         NOP
;
ONTIME:  LDA     LEDON            ; load loop counter
DELAY:   DECA
         BNE     DELAY            ; loop until ACC = 00
;
         LDA     #0FFH
         STA     PBDAT            ; turn all LED'S OFF
;
CLOCK:   BRCLR   4,PBDAT,CLK1     ; branch if bit 4 of Port B = 0; tag test is
;                                 ; being requested. This forces the execution
;                                 ; of the hourly calculations once every 2.5 sec.
;
;
         INC     TWSEC            ; increment seconds counter
         LDA     TWSEC
         CMP     SECMAX
         BLO     RETJMP           ; branch if a minute has not passed
;
         LDA     #00H             ; otherwise,
         STA     TWSEC            ; 2.5 second counter = 00
;
         INC     MIN              ; increment minutes counter
         LDA     MIN
         CMP     MINMAX
         BLO     RETJMP           ; branch if an hour has not passed
;
         LDA     #00H             ; otherwise,
         STA     MIN              ; minute counter = 00
         BRA     CLK1
;
RETJMP:  JMP     TIMRET
;
;
CLK1:    JSR     DATSTR           ; MOVE ACTIVITY COUNT TO DATA BASE AREA OF RAM
;
;
         LDA     ACTSHF           ; load number of right shifts
RSHFT:   LSR     ACTHI
         ROR     ACTLO            ; activity count = activity count / 2
         DECA
         BNE     RSHFT            ; loop until done
;                                 ; result is assumed to be 8 bits or less
         LDX     FLPNT            ; load file pointer
         LDA     ACTLO
         STA     ,X               ; move activity count to activity file
;
         LDA     #00H
         STA     ACTLO
         STA     ACTHI            ; Activity Counter = 0000
;
; Compute activity rate
;
         STA     TOTLO
         STA     TOTHI            ; zero summing register
;
         LDA     SUMCNT
         STA     CNTR             ; initialize sum counter
;
ACT2:    LDA     ,X               ; get an activity
         ADD     TOTLO
         STA     TOTLO
;
         LDA     TOTHI
         ADC     #00H             ; increment high bits in Carry was set by
         STA     TOTHI            ; previous ADD
;
         DEC     CNTR
         BNE     ACT3             ; branch if most recent activities have
;                                 ; not been summed
         STA     SUMHI            ; otherwise, save recent activity
         LDA     TOTLO
```

```
        STA     SUMLO
;
        LDA     #00H
        STA     TOTHI           ; zero summing register for total
        STA     TOTLO           ; of baseline activity
;
ACT3:   DECX                    ; decrement index
        CPX     #0FH
        BHI     ACT4            ; branch if index > 0FH
;
        LDX     FILTOP          ; otherwise reset index to top of file
;
ACT4:   CPX     FLPNT
        BNE     ACT2            ; branch if all activities have not been summed
;
        LDA     SUMSHF          ; load number of left shifts
LSHFT:  ASL     SUMLO
        ROL     SUMHI           ; SUM = SUM * 2
        DECA
        BNE     LSHFT           ; loop until done
;
        LDX     #00H
DIV:    LDA     SUMLO
        SUB     TOTLO
        STA     SUMLO
;
        LDA     SUMHI
        SBC     TOTHI
        STA     SUMHI           ; division by subtraction
;
        BLO     DIVEND          ; branch if result is negative
;
        INCX                    ; otherwise, increment division loop counter
        CPX     LMT4

BLO     DIV             ; branch if counter < LMT4
;
DIVEND: CPX     RATE
        BLS     PNTINC          ; branch if divison counter <= RATE
;
        STX     RATE            ; otherwise, save new RATE
;
PNTINC: LDX     FLPNT
        INCX                    ; increment file pointer
        CPX     FILTOP
        BLS     ACT1            ; branch if file pointer < 40H
;                                 otherwise
        LDX     #10H            ; reset file pointer
ACT1:   STX     FLPNT
;
TIMRET: BCLR    7,TIMCON        ; clear Timer interrupt pending
        RTI
;
;
;
; Routine for servicing an External interrupt (activity switch closure)
;
;
SWITCH: LDA     ACTLO
        ADD     #01H            ; increment lower bits of activity counter
        STA     ACTLO
;
        LDA     ACTHI
        ADC     #00H            ; increment high bits if carry was set by
                                ; previous ADD
        STA     ACTHI
;
        BSET    0,PADAT         ; reset external latch
        BCLR    0,PADAT
;
        RTI
;
;
```

; Serial data transmission routine
; 1 start bit, 8 bits of data, no parity, 2 or more stop bits
;

```
XMIT:   BCLR    0,PBDAT         ; turn LED 1 ON (start bit)
        LSRA                    ; move bit 0 to Carry
        ROL     PBDAT           ; move bit 0 to LED 1
        LSRA                    ; move bit 1 to Carry
        ROL     PBDAT           ; move bit 1 to LED 1
        LSRA                    ; move bit 2 to Carry
        ROL     PBDAT           ; move bit 2 to LED 1
        LSRA                    ; move bit 3 to Carry
        ROL     PBDAT           ; move bit 3 to LED 1
        NOP                     ; delay, help match bit rate to SIO baud rate
        LSRA                    ; move bit 4 to Carry
        ROL     PBDAT           ; move bit 4 to LED 1
        LSRA                    ; move bit 5 to Carry
        ROL     PBDAT           ; move bit 5 to LED 1
        LSRA                    ; move bit 6 to Carry
        ROL     PBDAT           ; move bit 6 to LED 1
        LSRA                    ; move bit 7 to Carry
        ROL     PBDAT           ; move bit 7 to LED 1
        NOP
        NOP                     ; delay, generate proper bit 7 transmitt time
        BSET    0,PBDAT         ; turn LED 1 OFF (stop bits)
        RTS
```

;
;
; Routine which dumps the contents of memory locations 100H to 5FFH.
; Required for research model tag only.
;

```
DUMP:   LDA     #01H
DMPLP:  STA     INDXA + 1       ; store high byte of 16 bit offset
        STA     INDXB + 1       ; store high byte of 16 bit offset LDX     #00             ; initialize pointer
        STX     CRCHI
        STX     CRCLO           ; initialize CRC check bytes INDXA:  LDA     0100H,X
        ADD     CRCLO
        STA     CRCLO           ; add data to previous sum
        LDA     CRCHI
        ADC     #00H            ; increment high byte if carry was set
                                ; by previous ADD
        STA     CRCHI INDXB:  LDA     0100H,X         ; get data byte
        JSR     XMIT            ; serially transmitt data
        INCX                    ; increment pointer
        BNE     INDXA           ; branch if 256 bytes have not been transmitted LDA     CRCLO           ; otherwise,
        JSR     XMIT            ; transmitt CRC check byte
        LDA     CRCHI
        JSR     XMIT            ; transmitt CRC check byte LDA     INDXA + 1
        INCA                    ; increment extended index pointer CMP     #06H
        BLO     DMPLP           ; branch if all of memory has not been transmitt,
        RTS                     ; otherwise, routine is complete
```

;
;
; Establish interrupt vector table
;

```
        ORG     07F6H
        DW      TIMINT          ; interrupt vector for Timer from WAIT only
```

```
DW      TIMINT          ; interrupt vector for Timer
DW      SWITCH          ; interrupt vector for External Interrupt
DW      RESET           ; interrupt vector for Software Interrupt
DW      RESET           ; interrupt vector for Reset
;
;
END     RESET
```

I claim:

1. A self-contained tag for indicating estrus in an animal to which it is attached, the combination comprising:
   a motion detector for sensing significant animal movements;
   current activity counter means coupled to the motion detector for accumulating a count indicative of the animal activity over a current time period;
   reference activity counter means coupled to the motion detector for accumulating a count indicative of the animal activity over a reference time period;
   indicator means for providing an indication of increased animal activity when energized; and
   comparator means coupled to the current activity counter means and the reference activity counter means for comparing the magnitudes of their counts and energizing the indicator means when the ratio of the current activity over the reference activity exceeds a preselected amount.

2. The tag as recited in claim 1 in which the indicator means is a light emitting diode.

3. The tag as recited in claim 1 in which a magnetically operable reed switch is coupled to said current activity counter means for resetting the same when a magnet is placed adjacent the tag.

4. The tag as recited in claim 1 which includes externally operable reset means coupled to the comparator means for de-energizing the indicator means.

5. A self-contained tag for indicating estrus in an animal to which it is attached, the combination comprising:
   a motion detector for sensing significant animal movements;
   indicator means for providing an indication of increased animal activity when energized;
   processor means having an input coupled to the motion detector and an output coupled to the indicator means, the processor means including memory means for storing a current activity count and an activity table which is comprised of a series of prior activity counts, and timer means for establishing a sample period, wherein the processor also includes:
   (a) means for incrementing the current activity count each time a significant animal motion is detected;
   (b) means for storing the current activity count in the activity table at the end of each of said sample periods;
   (c) means for calculating a reference activity from a first selected set of activity counts stored in the activity table;
   (d) means for calculating a current activity number from a second selected set of activity counts stored in the activity table;
   (e) means for calculating a rate number which indicates the ratio of the current activity count to the reference activity; and
   (f) means for energizing the indicator means when the calculated rate number exceeds a preset value.

6. The tag as recited in claim 5 in which a reed switch is coupled to said processor means and is operable to reset the same when a magnet is positioned near the tag.

7. The tag as recited in claim 6 in which the processor means also includes means operable when reset for sequentially reading the activity count values stored in the activity table and serially outputting each value to the indicator means.

8. The tag as recited in claim 5 in which there is a second indicator means coupled to an output on the processor means and the second indicator is energized when the calculated rate number exceeds a second preset value.

9. The tag as recited in claim 8 in which said first and second indicator means are light emitting diodes.

10. The tag as recited in claim 5 in which the means for calculating a reference activity calculates by summing the activity counts in said first selected set of activity counts and the means for calculating a current activity number calculates by summing the activity counts in said second selected set of activity counts.

11. The tag as recited in claim 10 in which said first selected set of activity counts is selected by said means for calculating a reference activity to include activity counts accumulated over a relatively long time period, and in which said second selected set of activity counts is selected by said means for calculating a current activity number to include activity counts accumulated over a recent, relatively short time period.

* * * * *